(12) United States Patent
Spivey

(10) Patent No.: US 8,211,125 B2
(45) Date of Patent: Jul. 3, 2012

(54) STERILE APPLIANCE DELIVERY DEVICE FOR ENDOSCOPIC PROCEDURES

(75) Inventor: James T. Spivey, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 946 days.

(21) Appl. No.: 12/192,372

(22) Filed: Aug. 15, 2008

(65) Prior Publication Data

US 2010/0042045 A1 Feb. 18, 2010
US 2010/0331774 A2 Dec. 30, 2010

(51) Int. Cl.
*A61B 17/08* (2006.01)
(52) U.S. Cl. .................... 606/151; 606/213; 606/108
(58) Field of Classification Search .................. 606/151, 606/127, 106, 110, 114, 128, 138, 139, 191–194, 606/213; 604/19, 93.01, 540, 57.59–64, 604/48, 500, 506, 27, 73, 408, 262, 140–148, 604/164.05; 600/29, 30, 37; 623/23.72, 623/23.75, 23.76; 206/363, 438, 441
See application file for complete search history.

(56) References Cited

U.S. PATENT DOCUMENTS

| 645,576 | A | 3/1900 | Telsa |
|---|---|---|---|
| 649,621 | A | 5/1900 | Tesla |
| 787,412 | A | 4/1905 | Tesla |
| 1,127,948 | A | 2/1915 | Wappler |
| 1,482,653 | A | 2/1924 | Lilly |
| 1,625,602 | A | 4/1927 | Gould et al. |
| 2,028,635 | A | 1/1936 | Wappler |
| 2,031,682 | A | 2/1936 | Wappler et al. |
| 2,113,246 | A | 4/1938 | Wappler |
| 2,155,365 | A | 4/1939 | Rankin |
| 2,191,858 | A | 2/1940 | Moore |
| 2,196,620 | A | 4/1940 | Attarian |
| 2,388,137 | A | 10/1945 | Graumlich |
| 2,493,108 | A | 1/1950 | Casey, Jr. |
| 2,504,152 | A | 4/1950 | Riker et al. |
| 2,938,382 | A | 5/1960 | De Graaf |
| 2,952,206 | A | 9/1960 | Becksted |
| 3,069,195 | A | 12/1962 | Buck |
| 3,170,471 | A | 2/1965 | Schnitzer |
| 3,435,824 | A | 4/1969 | Gamponia |
| 3,470,876 | A | 10/1969 | Barchilon |
| 3,595,239 | A | 7/1971 | Petersen |
| 3,669,487 | A | 6/1972 | Roberts et al. |
| 3,746,881 | A | 7/1973 | Fitch et al. |

(Continued)

FOREIGN PATENT DOCUMENTS

AU 666310 B2 2/1996

(Continued)

OTHER PUBLICATIONS

International Search Report for PCT/US2009/053536, Jan. 21, 2010 (11 pages).

(Continued)

*Primary Examiner* — Corrine M McDermott
*Assistant Examiner* — Todd J Scherbel

(57) ABSTRACT

A surgical device comprising a container and a tether used for delivering a sterile appliance into a body cavity during endoscopic procedures. Once positioned in the body cavity, a force is applied to the container through the tether. The force opens the container and releases the sterile appliance into the body cavity. In various embodiments, gas or liquid may be used to open the container.

16 Claims, 5 Drawing Sheets

U.S. PATENT DOCUMENTS

| | | |
|---|---|---|
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A * | 2/1986 | Frisbie ................. 606/108 |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A * | 9/1992 | Fernandez ................. 606/151 |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A * | 5/1994 | Churinetz et al. ............... 604/57 |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |

| Patent | Date | Inventor |
|---|---|---|
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A * | 7/1997 | Shah ................................ 2/167 |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,911,737 A | 6/1999 | Lee et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |

| | | | | | | |
|---|---|---|---|---|---|---|
| 5,928,255 | A | 7/1999 | Meade et al. | 6,264,664 B1 | 7/2001 | Avellanet |
| 5,928,266 | A | 7/1999 | Kontos | 6,270,497 B1 | 8/2001 | Sekino et al. |
| 5,936,536 | A | 8/1999 | Morris | 6,270,505 B1 | 8/2001 | Yoshida et al. |
| 5,944,718 | A | 8/1999 | Austin et al. | 6,277,136 B1 | 8/2001 | Bonutti |
| 5,951,549 | A | 9/1999 | Richardson et al. | 6,283,963 B1 | 9/2001 | Regula |
| 5,954,720 | A | 9/1999 | Wilson et al. | 6,293,909 B1 | 9/2001 | Chu et al. |
| 5,954,731 | A | 9/1999 | Yoon | 6,293,952 B1 | 9/2001 | Brosens et al. |
| 5,957,943 | A | 9/1999 | Vaitekunas | 6,296,630 B1 | 10/2001 | Altman et al. |
| 5,957,953 | A | 9/1999 | DiPoto et al. | 6,322,578 B1 | 11/2001 | Houle et al. |
| 5,971,995 | A | 10/1999 | Rousseau | 6,326,177 B1 | 12/2001 | Schoenbach et al. |
| 5,976,074 | A | 11/1999 | Moriyama | 6,328,730 B1 | 12/2001 | Harkrider, Jr. |
| 5,976,075 | A | 11/1999 | Beane et al. | 6,350,267 B1 | 2/2002 | Stefanchik |
| 5,976,130 | A | 11/1999 | McBrayer et al. | 6,350,278 B1 * | 2/2002 | Lenker et al. ................. 623/1.12 |
| 5,976,131 | A | 11/1999 | Guglielmi et al. | 6,352,503 B1 | 3/2002 | Matsui et al. |
| 5,980,539 | A | 11/1999 | Kontos | 6,352,543 B1 | 3/2002 | Cole |
| 5,980,556 | A | 11/1999 | Giordano et al. | 6,355,035 B1 | 3/2002 | Manushakian |
| 5,984,938 | A | 11/1999 | Yoon | 6,361,534 B1 | 3/2002 | Chen et al. |
| 5,984,939 | A | 11/1999 | Yoon | 6,371,956 B1 | 4/2002 | Wilson et al. |
| 5,989,182 | A | 11/1999 | Hori et al. | 6,379,366 B1 | 4/2002 | Fleischman et al. |
| 5,993,447 | A | 11/1999 | Blewett et al. | 6,383,195 B1 | 5/2002 | Richard |
| 5,997,555 | A | 12/1999 | Kontos | 6,383,197 B1 | 5/2002 | Conlon et al. |
| 6,001,120 | A | 12/1999 | Levin | 6,391,029 B1 | 5/2002 | Hooven et al. |
| 6,004,269 | A | 12/1999 | Crowley et al. | 6,402,735 B1 | 6/2002 | Langevin |
| 6,004,330 | A | 12/1999 | Middleman et al. | 6,406,440 B1 | 6/2002 | Stefanchik |
| 6,007,566 | A | 12/1999 | Wenstrom, Jr. | 6,409,733 B1 | 6/2002 | Conlon et al. |
| 6,010,515 | A | 1/2000 | Swain et al. | 6,427,089 B1 | 7/2002 | Knowlton |
| 6,012,494 | A | 1/2000 | Balazs | 6,431,500 B1 | 8/2002 | Jacobs et al. |
| 6,017,356 | A | 1/2000 | Frederick et al. | 6,443,970 B1 | 9/2002 | Schulze et al. |
| 6,019,770 | A | 2/2000 | Christoudias | 6,443,988 B2 | 9/2002 | Felt et al. |
| 6,024,708 | A | 2/2000 | Bales et al. | 6,447,511 B1 | 9/2002 | Slater |
| 6,024,747 | A | 2/2000 | Kontos | 6,447,523 B1 | 9/2002 | Middleman et al. |
| 6,027,522 | A | 2/2000 | Palmer | 6,454,783 B1 | 9/2002 | Piskun |
| 6,030,365 | A | 2/2000 | Laufer | 6,454,785 B2 | 9/2002 | De Hoyos Garza |
| 6,030,634 | A | 2/2000 | Wu et al. | 6,458,076 B1 | 10/2002 | Pruitt |
| 6,033,399 | A | 3/2000 | Gines | 6,464,701 B1 | 10/2002 | Hooven et al. |
| 6,036,685 | A | 3/2000 | Mueller | 6,464,702 B2 | 10/2002 | Schulze et al. |
| 6,053,927 | A | 4/2000 | Hamas | 6,475,104 B1 | 11/2002 | Lutz et al. |
| 6,066,160 | A | 5/2000 | Colvin et al. | 6,485,411 B1 | 11/2002 | Konstorum et al. |
| 6,066,603 | A | 5/2000 | Suzuki | 6,489,745 B1 | 12/2002 | Koreis |
| 6,068,629 | A | 5/2000 | Haissaguerre et al. | 6,491,626 B1 | 12/2002 | Stone et al. |
| 6,071,233 | A | 6/2000 | Ishikawa et al. | 6,491,627 B1 | 12/2002 | Komi |
| 6,074,408 | A | 6/2000 | Freeman | 6,491,691 B1 | 12/2002 | Morley et al. |
| 6,086,530 | A | 7/2000 | Mack | 6,493,590 B1 | 12/2002 | Wessman et al. |
| 6,090,108 | A | 7/2000 | McBrayer et al. | 6,494,893 B2 | 12/2002 | Dubrul et al. |
| 6,096,046 | A | 8/2000 | Weiss | 6,500,176 B1 | 12/2002 | Truckai et al. |
| 6,102,926 | A | 8/2000 | Tartaglia et al. | 6,503,192 B1 | 1/2003 | Ouchi |
| 6,106,473 | A | 8/2000 | Violante et al. | 6,506,190 B1 | 1/2003 | Walshe |
| 6,109,852 | A | 8/2000 | Shahinpoor et al. | 6,508,827 B1 | 1/2003 | Manhes |
| 6,110,154 | A | 8/2000 | Shimomura et al. | 6,520,954 B2 | 2/2003 | Ouchi |
| 6,110,183 | A | 8/2000 | Cope | 6,543,456 B1 | 4/2003 | Freeman |
| 6,113,593 | A | 9/2000 | Tu et al. | 6,551,270 B1 | 4/2003 | Bimbo et al. |
| 6,117,144 | A | 9/2000 | Nobles et al. | 6,554,829 B2 | 4/2003 | Schulze et al. |
| 6,117,158 | A | 9/2000 | Measamer et al. | 6,558,384 B2 | 5/2003 | Mayenberger |
| 6,139,555 | A | 10/2000 | Hart et al. | 6,562,035 B1 | 5/2003 | Levin |
| 6,146,391 | A | 11/2000 | Cigaina | 6,562,052 B2 | 5/2003 | Nobles et al. |
| 6,148,222 | A | 11/2000 | Ramsey, III | 6,569,159 B1 | 5/2003 | Edwards et al. |
| 6,149,653 | A | 11/2000 | Deslauriers | 6,572,629 B2 | 6/2003 | Kalloo et al. |
| 6,149,662 | A | 11/2000 | Pugliesi et al. | 6,572,635 B2 | 6/2003 | Bonutti |
| 6,159,200 | A | 12/2000 | Verdura et al. | 6,575,988 B2 | 6/2003 | Rousseau |
| 6,165,184 | A | 12/2000 | Verdura et al. | 6,579,311 B1 | 6/2003 | Makower |
| 6,168,570 | B1 | 1/2001 | Ferrera | 6,585,642 B2 | 7/2003 | Christopher |
| 6,168,605 | B1 | 1/2001 | Measamer et al. | 6,585,717 B1 | 7/2003 | Wittenberger et al. |
| 6,170,130 | B1 | 1/2001 | Hamilton et al. | 6,592,559 B1 | 7/2003 | Pakter et al. |
| 6,179,776 | B1 | 1/2001 | Adams et al. | 6,592,603 B2 | 7/2003 | Lasner |
| 6,179,837 | B1 | 1/2001 | Hooven | 6,602,262 B2 | 8/2003 | Griego et al. |
| 6,183,420 | B1 | 2/2001 | Douk et al. | 6,605,105 B1 | 8/2003 | Cuschieri et al. |
| 6,190,353 | B1 | 2/2001 | Makower et al. | 6,610,072 B1 | 8/2003 | Christy et al. |
| 6,190,384 | B1 | 2/2001 | Ouchi | 6,610,074 B2 | 8/2003 | Santilli |
| 6,190,399 | B1 | 2/2001 | Palmer et al. | 6,620,193 B1 | 9/2003 | Lau et al. |
| 6,203,533 | B1 | 3/2001 | Ouchi | 6,623,448 B2 | 9/2003 | Slater |
| 6,206,872 | B1 | 3/2001 | Lafond et al. | 6,626,919 B1 | 9/2003 | Swanstrom |
| 6,206,877 | B1 | 3/2001 | Kese et al. | 6,632,229 B1 | 10/2003 | Yamanouchi |
| 6,214,007 | B1 | 4/2001 | Anderson | 6,638,286 B1 | 10/2003 | Burbank et al. |
| 6,228,096 | B1 | 5/2001 | Marchand | 6,652,521 B2 | 11/2003 | Schulze |
| 6,234,958 | B1 | 5/2001 | Snoke et al. | 6,652,551 B1 | 11/2003 | Heiss |
| 6,245,079 | B1 | 6/2001 | Nobles et al. | 6,656,194 B1 | 12/2003 | Gannoe et al. |
| 6,246,914 | B1 | 6/2001 | de la Rama et al. | 6,663,641 B1 | 12/2003 | Kovac et al. |
| 6,258,064 | B1 | 7/2001 | Smith et al. | 6,666,854 B1 | 12/2003 | Lange |
| 6,261,242 | B1 | 7/2001 | Roberts et al. | 6,672,338 B1 | 1/2004 | Esashi et al. |

| Patent | Date | Name | Patent | Date | Name |
|---|---|---|---|---|---|
| 6,673,058 B2 | 1/2004 | Snow | 7,000,818 B2 | 2/2006 | Shelton, IV et al. |
| 6,673,087 B1 | 1/2004 | Chang et al. | 7,001,341 B2 | 2/2006 | Gellman et al. |
| 6,679,882 B1 | 1/2004 | Kornerup | 7,008,375 B2 | 3/2006 | Weisel |
| 6,685,628 B2 | 2/2004 | Vu | 7,009,634 B2 | 3/2006 | Iddan et al. |
| 6,685,724 B1 | 2/2004 | Haluck | 7,010,340 B2 | 3/2006 | Scarantino et al. |
| 6,692,445 B2 | 2/2004 | Roberts et al. | 7,020,531 B1 | 3/2006 | Colliou et al. |
| 6,692,462 B2 | 2/2004 | Mackenzie et al. | 7,025,580 B2 | 4/2006 | Heagy et al. |
| 6,699,180 B2 | 3/2004 | Kobayashi | 7,029,435 B2 | 4/2006 | Nakao |
| 6,699,256 B1 | 3/2004 | Logan et al. | 7,029,438 B2 | 4/2006 | Morin et al. |
| 6,699,263 B2 | 3/2004 | Cope | 7,029,450 B2 | 4/2006 | Gellman |
| 6,706,018 B2 | 3/2004 | Westlund et al. | 7,035,680 B2 | 4/2006 | Partridge et al. |
| 6,708,066 B2 | 3/2004 | Herbst et al. | 7,037,290 B2 | 5/2006 | Gardeski et al. |
| 6,709,445 B2 | 3/2004 | Boebel et al. | 7,041,052 B2 | 5/2006 | Saadat et al. |
| 6,716,226 B2 | 4/2004 | Sixto, Jr. et al. | 7,052,489 B2 | 5/2006 | Griego et al. |
| 6,736,822 B2 | 5/2004 | McClellan et al. | 7,060,024 B2 | 6/2006 | Long et al. |
| 6,740,030 B2 | 5/2004 | Martone et al. | 7,060,025 B2 | 6/2006 | Long et al. |
| 6,743,240 B2 | 6/2004 | Smith et al. | 7,063,697 B2 | 6/2006 | Slater |
| 6,749,560 B1 | 6/2004 | Konstorum et al. | 7,063,715 B2 | 6/2006 | Onuki et al. |
| 6,749,609 B1 | 6/2004 | Lunsford et al. | 7,066,879 B2 | 6/2006 | Fowler et al. |
| 6,752,811 B2 | 6/2004 | Chu et al. | 7,066,936 B2 | 6/2006 | Ryan |
| 6,752,822 B2 | 6/2004 | Jespersen | 7,070,602 B2 | 7/2006 | Smith et al. |
| 6,761,685 B2 | 7/2004 | Adams et al. | 7,076,305 B2 | 7/2006 | Imran et al. |
| 6,761,718 B2 | 7/2004 | Madsen | 7,083,618 B2 | 8/2006 | Couture et al. |
| 6,773,434 B2 | 8/2004 | Ciarrocca | 7,083,620 B2 | 8/2006 | Jahns et al. |
| 6,780,151 B2 | 8/2004 | Grabover et al. | 7,083,629 B2 | 8/2006 | Weller et al. |
| 6,780,352 B2 | 8/2004 | Jacobson | 7,083,635 B2 | 8/2006 | Ginn |
| 6,783,491 B2 | 8/2004 | Saadat et al. | 7,087,071 B2 | 8/2006 | Nicholas et al. |
| 6,786,864 B2 | 9/2004 | Matsuura et al. | 7,090,673 B2 | 8/2006 | Dycus et al. |
| 6,790,173 B2 | 9/2004 | Saadat et al. | 7,090,685 B2 | 8/2006 | Kortenbach et al. |
| 6,795,728 B2 | 9/2004 | Chornenky et al. | 7,093,518 B2 | 8/2006 | Gmeilbauer |
| 6,800,056 B2 | 10/2004 | Tartaglia et al. | 7,101,371 B2 | 9/2006 | Dycus et al. |
| 6,808,491 B2 | 10/2004 | Kortenbach et al. | 7,101,372 B2 | 9/2006 | Dycus et al. |
| 6,824,548 B2 | 11/2004 | Smith et al. | 7,101,373 B2 | 9/2006 | Dycus et al. |
| 6,836,688 B2 | 12/2004 | Ingle et al. | 7,105,000 B2 | 9/2006 | McBrayer |
| 6,837,847 B2 | 1/2005 | Ewers et al. | 7,105,005 B2 | 9/2006 | Blake |
| 6,843,794 B2 | 1/2005 | Sixto, Jr. et al. | 7,108,703 B2 | 9/2006 | Danitz et al. |
| 6,861,250 B1 | 3/2005 | Cole et al. | 7,112,208 B2 | 9/2006 | Morris et al. |
| 6,866,627 B2 | 3/2005 | Nozue | 7,115,092 B2 | 10/2006 | Park et al. |
| 6,878,106 B1 | 4/2005 | Herrmann | 7,117,703 B2 | 10/2006 | Kato et al. |
| 6,878,110 B2 | 4/2005 | Yang et al. | 7,118,531 B2 | 10/2006 | Krill |
| 6,881,216 B2 | 4/2005 | Di Caprio et al. | 7,118,578 B2 | 10/2006 | West, Jr. et al. |
| 6,884,213 B2 | 4/2005 | Raz et al. | 7,118,587 B2 | 10/2006 | Dycus et al. |
| 6,887,255 B2 | 5/2005 | Shimm | 7,128,708 B2 | 10/2006 | Saadat et al. |
| 6,889,089 B2 | 5/2005 | Behl et al. | RE39,415 E | 11/2006 | Bales et al. |
| 6,896,683 B1 | 5/2005 | Gadberry et al. | 7,131,978 B2 | 11/2006 | Sancoff et al. |
| 6,896,692 B2 | 5/2005 | Ginn et al. | 7,131,979 B2 | 11/2006 | DiCarlo et al. |
| 6,908,427 B2 | 6/2005 | Fleener et al. | 7,131,980 B1 | 11/2006 | Field et al. |
| 6,908,476 B2 | 6/2005 | Jud et al. | 7,137,980 B2 | 11/2006 | Buysse et al. |
| 6,916,284 B2 | 7/2005 | Moriyama | 7,137,981 B2 | 11/2006 | Long |
| 6,918,871 B2 | 7/2005 | Schulze | 7,146,984 B2 | 12/2006 | Stack et al. |
| 6,926,725 B2 | 8/2005 | Cooke et al. | 7,147,650 B2 | 12/2006 | Lee |
| 6,932,810 B2 | 8/2005 | Ryan | 7,150,097 B2 | 12/2006 | Sremcich et al. |
| 6,932,824 B1 | 8/2005 | Roop et al. | 7,153,321 B2 | 12/2006 | Andrews |
| 6,932,827 B2 | 8/2005 | Cole | 7,163,525 B2 | 1/2007 | Franer |
| 6,939,327 B2 * | 9/2005 | Hall et al. ............ 604/164.05 | 7,172,714 B2 | 2/2007 | Jacobson |
| 6,942,613 B2 | 9/2005 | Ewers et al. | 7,179,254 B2 | 2/2007 | Pendekanti et al. |
| 6,945,472 B2 | 9/2005 | Wuttke et al. | 7,188,627 B2 | 3/2007 | Nelson et al. |
| 6,945,979 B2 | 9/2005 | Kortenbach et al. | 7,195,612 B2 | 3/2007 | Van Sloten et al. |
| 6,958,035 B2 | 10/2005 | Friedman et al. | 7,195,631 B2 | 3/2007 | Dumbauld |
| 6,960,162 B2 | 11/2005 | Saadat et al. | 7,204,820 B2 | 4/2007 | Akahoshi |
| 6,960,163 B2 | 11/2005 | Ewers et al. | 7,208,005 B2 | 4/2007 | Frecker et al. |
| 6,962,587 B2 | 11/2005 | Johnson et al. | 7,211,092 B2 | 5/2007 | Hughett |
| 6,964,662 B2 | 11/2005 | Kidooka | 7,220,227 B2 | 5/2007 | Sasaki et al. |
| 6,966,909 B2 | 11/2005 | Marshall et al. | 7,223,272 B2 | 5/2007 | Francese et al. |
| 6,966,919 B2 | 11/2005 | Sixto, Jr. et al. | 7,232,414 B2 | 6/2007 | Gonzalez |
| 6,967,462 B1 | 11/2005 | Landis | 7,232,445 B2 | 6/2007 | Kortenbach et al. |
| 6,971,988 B2 | 12/2005 | Orban, III | 7,241,290 B2 | 7/2007 | Doyle et al. |
| 6,972,017 B2 | 12/2005 | Smith et al. | 7,244,228 B2 | 7/2007 | Lubowski |
| 6,974,411 B2 | 12/2005 | Belson | 7,250,027 B2 | 7/2007 | Barry |
| 6,976,992 B2 | 12/2005 | Sachatello et al. | 7,252,660 B2 | 8/2007 | Kunz |
| 6,984,203 B2 | 1/2006 | Tartaglia et al. | 7,255,675 B2 | 8/2007 | Gertner et al. |
| 6,984,205 B2 | 1/2006 | Gazdzinski | 7,270,663 B2 | 9/2007 | Nakao |
| 6,986,774 B2 | 1/2006 | Middleman et al. | 7,294,139 B1 | 11/2007 | Gengler |
| 6,988,987 B2 | 1/2006 | Ishikawa et al. | 7,301,250 B2 | 11/2007 | Cassel |
| 6,989,028 B2 | 1/2006 | Lashinski et al. | 7,306,597 B2 | 12/2007 | Manzo |
| 6,991,627 B2 | 1/2006 | Madhani et al. | 7,308,828 B2 | 12/2007 | Hashimoto |
| 6,991,631 B2 | 1/2006 | Woloszko et al. | 7,318,802 B2 | 1/2008 | Suzuki et al. |
| 6,994,708 B2 | 2/2006 | Manzo | 7,320,695 B2 | 1/2008 | Carroll |
| 6,997,931 B2 | 2/2006 | Sauer et al. | 7,322,934 B2 | 1/2008 | Miyake et al. |

| | | | | | | |
|---|---|---|---|---|---|---|
| 7,323,006 B2 | 1/2008 | Andreas et al. | | 8,075,587 B2 | 12/2011 | Ginn |
| 7,329,256 B2 | 2/2008 | Johnson et al. | | 2001/0049497 A1 | 12/2001 | Kalloo et al. |
| 7,329,257 B2 | 2/2008 | Kanehira et al. | | 2002/0022771 A1 | 2/2002 | Diokno et al. |
| 7,329,383 B2 | 2/2008 | Stinson | | 2002/0022857 A1 | 2/2002 | Goldsteen et al. |
| 7,344,536 B1 | 3/2008 | Lunsford et al. | | 2002/0023353 A1 | 2/2002 | Ting-Kung |
| 7,352,387 B2 | 4/2008 | Yamamoto | | 2002/0029055 A1 | 3/2002 | Bonutti |
| 7,364,582 B2 | 4/2008 | Lee | | 2002/0042562 A1 | 4/2002 | Meron et al. |
| 7,371,215 B2 | 5/2008 | Colliou et al. | | 2002/0049439 A1 | 4/2002 | Mulier et al. |
| 7,381,216 B2 | 6/2008 | Buzzard et al. | | 2002/0068945 A1 | 6/2002 | Sixto, Jr. et al. |
| 7,393,322 B2 | 7/2008 | Wenchell | | 2002/0078967 A1 | 6/2002 | Sixto, Jr. et al. |
| 7,402,162 B2 | 7/2008 | Ouchi | | 2002/0082516 A1 | 6/2002 | Stefanchik |
| 7,404,791 B2 | 7/2008 | Linares et al. | | 2002/0091391 A1 | 7/2002 | Cole et al. |
| 7,413,563 B2 | 8/2008 | Corcoran et al. | | 2002/0095164 A1 | 7/2002 | Andreas et al. |
| 7,416,554 B2 | 8/2008 | Lam et al. | | 2002/0107530 A1 | 8/2002 | Sauer et al. |
| 7,422,590 B2 | 9/2008 | Kupferschmid et al. | | 2002/0133115 A1 | 9/2002 | Gordon et al. |
| 7,435,257 B2 | 10/2008 | Lashinski et al. | | 2002/0138086 A1 | 9/2002 | Sixto, Jr. et al. |
| 7,452,327 B2 | 11/2008 | Durgin et al. | | 2002/0147456 A1 | 10/2002 | Diduch et al. |
| 7,455,208 B2 | 11/2008 | Wales et al. | | 2002/0183591 A1 | 12/2002 | Matsuura et al. |
| 7,468,066 B2 | 12/2008 | Vargas et al. | | 2003/0023255 A1 | 1/2003 | Miles et al. |
| 7,488,295 B2 | 2/2009 | Burbank et al. | | 2003/0036679 A1 | 2/2003 | Kortenbach et al. |
| 7,497,867 B2 | 3/2009 | Lasner et al. | | 2003/0069602 A1 | 4/2003 | Jacobs et al. |
| 7,507,200 B2 | 3/2009 | Okada | | 2003/0083681 A1 | 5/2003 | Moutafis et al. |
| 7,524,281 B2 | 4/2009 | Chu et al. | | 2003/0114732 A1 | 6/2003 | Webler et al. |
| 7,524,302 B2 | 4/2009 | Tower | | 2003/0120257 A1 | 6/2003 | Houston et al. |
| 7,534,228 B2 | 5/2009 | Williams | | 2003/0124009 A1 | 7/2003 | Ravi et al. |
| 7,540,872 B2 | 6/2009 | Schechter et al. | | 2003/0130564 A1 | 7/2003 | Martone et al. |
| 7,544,203 B2 | 6/2009 | Chin et al. | | 2003/0130656 A1 | 7/2003 | Levin |
| 7,548,040 B2 | 6/2009 | Lee et al. | | 2003/0158521 A1 | 8/2003 | Ameri |
| 7,549,564 B2 | 6/2009 | Boudreaux | | 2003/0167062 A1 | 9/2003 | Gambale et al. |
| 7,553,278 B2 | 6/2009 | Kucklick | | 2003/0171651 A1 | 9/2003 | Page et al. |
| 7,553,298 B2 | 6/2009 | Hunt et al. | | 2003/0176880 A1 | 9/2003 | Long et al. |
| 7,559,887 B2 | 7/2009 | Dannan | | 2003/0191497 A1 | 10/2003 | Cope |
| 7,559,916 B2 | 7/2009 | Smith et al. | | 2003/0195565 A1 | 10/2003 | Bonutti |
| 7,560,006 B2 | 7/2009 | Rakos et al. | | 2003/0216611 A1 | 11/2003 | Vu |
| 7,561,916 B2 | 7/2009 | Hunt et al. | | 2003/0216615 A1 | 11/2003 | Ouchi |
| 7,566,334 B2 | 7/2009 | Christian et al. | | 2003/0220545 A1 | 11/2003 | Ouchi |
| 7,575,144 B2 | 8/2009 | Ortiz et al. | | 2003/0225312 A1 | 12/2003 | Suzuki et al. |
| 7,575,548 B2 | 8/2009 | Takemoto et al. | | 2003/0225332 A1 | 12/2003 | Okada et al. |
| 7,579,550 B2 | 8/2009 | Dayton et al. | | 2003/0229269 A1 | 12/2003 | Humphrey |
| 7,582,096 B2 | 9/2009 | Gellman et al. | | 2003/0229371 A1 | 12/2003 | Whitworth |
| 7,588,177 B2 | 9/2009 | Racenet | | 2003/0236549 A1 | 12/2003 | Bonadio et al. |
| 7,588,557 B2 | 9/2009 | Nakao | | 2004/0002683 A1 | 1/2004 | Nicholson et al. |
| 7,618,398 B2 | 11/2009 | Holman et al. | | 2004/0002735 A1 | 1/2004 | Lizardi et al. |
| 7,632,250 B2 | 12/2009 | Smith et al. | | 2004/0034369 A1 | 2/2004 | Sauer et al. |
| 7,635,373 B2 | 12/2009 | Ortiz | | 2004/0098007 A1 | 5/2004 | Heiss |
| 7,637,903 B2 | 12/2009 | Lentz et al. | | 2004/0101456 A1 | 5/2004 | Kuroshima et al. |
| 7,651,483 B2 | 1/2010 | Byrum et al. | | 2004/0116948 A1 | 6/2004 | Sixto, Jr. et al. |
| 7,651,509 B2 | 1/2010 | Bojarski et al. | | 2004/0127940 A1 | 7/2004 | Ginn et al. |
| 7,654,431 B2 | 2/2010 | Hueil et al. | | 2004/0133077 A1 | 7/2004 | Obenchain et al. |
| 7,662,089 B2 | 2/2010 | Okada et al. | | 2004/0133089 A1 | 7/2004 | Kilcoyne et al. |
| 7,666,180 B2 | 2/2010 | Holsten et al. | | 2004/0136779 A1 | 7/2004 | Bhaskar |
| 7,674,259 B2 | 3/2010 | Shadduck | | 2004/0138525 A1 | 7/2004 | Saadat et al. |
| 7,713,189 B2 | 5/2010 | Hanke | | 2004/0138529 A1 | 7/2004 | Wiltshire et al. |
| 7,713,270 B2 | 5/2010 | Suzuki | | 2004/0138587 A1 | 7/2004 | Lyons, IV |
| 7,736,374 B2 | 6/2010 | Vaughan et al. | | 2004/0161451 A1 | 8/2004 | Pierce et al. |
| 7,744,615 B2 | 6/2010 | Couture | | 2004/0186350 A1 | 9/2004 | Brenneman et al. |
| 7,758,577 B2 | 7/2010 | Nobis et al. | | 2004/0193009 A1 | 9/2004 | Jaffe et al. |
| 7,762,998 B2 | 7/2010 | Birk et al. | | 2004/0193146 A1 | 9/2004 | Lee et al. |
| 7,771,416 B2 | 8/2010 | Spivey et al. | | 2004/0193186 A1 | 9/2004 | Kortenbach et al. |
| 7,780,683 B2 | 8/2010 | Roue et al. | | 2004/0193188 A1 | 9/2004 | Francese |
| 7,780,691 B2 | 8/2010 | Stefanchik | | 2004/0193189 A1 | 9/2004 | Kortenbach et al. |
| 7,794,409 B2 | 9/2010 | Damarati | | 2004/0193200 A1 | 9/2004 | Dworschak et al. |
| 7,794,475 B2 | 9/2010 | Hess et al. | | 2004/0199052 A1 | 10/2004 | Banik et al. |
| 7,828,186 B2 | 11/2010 | Wales | | 2004/0210245 A1 | 10/2004 | Erickson et al. |
| 7,837,615 B2 | 11/2010 | Le et al. | | 2004/0215058 A1 | 10/2004 | Zirps et al. |
| 7,850,660 B2 | 12/2010 | Uth et al. | | 2004/0225183 A1 | 11/2004 | Michlitsch et al. |
| 7,857,183 B2 | 12/2010 | Shelton, IV | | 2004/0225186 A1 | 11/2004 | Horne, Jr. et al. |
| 7,862,546 B2 | 1/2011 | Conlon et al. | | 2004/0230095 A1 | 11/2004 | Stefanchik et al. |
| 7,867,216 B2 | 1/2011 | Wahr et al. | | 2004/0230096 A1 | 11/2004 | Stefanchik et al. |
| 7,892,220 B2 | 2/2011 | Faller et al. | | 2004/0230097 A1 | 11/2004 | Stefanchik et al. |
| 7,896,887 B2 * | 3/2011 | Rimbaugh et al. ............ 606/108 | | 2004/0230161 A1 | 11/2004 | Zeiner |
| 7,909,809 B2 | 3/2011 | Scopton et al. | | 2004/0249246 A1 | 12/2004 | Campos |
| 7,914,513 B2 | 3/2011 | Voorhees, Jr. | | 2004/0249367 A1 | 12/2004 | Saadat et al. |
| 7,918,869 B2 | 4/2011 | Saadat et al. | | 2004/0249394 A1 | 12/2004 | Morris et al. |
| 7,931,624 B2 | 4/2011 | Smith et al. | | 2004/0249443 A1 | 12/2004 | Shanley et al. |
| 7,945,332 B2 | 5/2011 | Schechter | | 2005/0004515 A1 | 1/2005 | Hart et al. |
| 7,947,000 B2 | 5/2011 | Vargas et al. | | 2005/0004592 A1 * | 1/2005 | Criscuolo ............ 606/190 |
| 7,955,298 B2 | 6/2011 | Carroll et al. | | 2005/0033265 A1 | 2/2005 | Engel et al. |
| 7,988,685 B2 | 8/2011 | Ziaie et al. | | 2005/0033277 A1 | 2/2005 | Clague et al. |

| | | |
|---|---|---|
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277942 A1* | 12/2005 | Kullas et al. ............... 606/99 |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |

| | | |
|---|---|---|
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |

| | | | | | | |
|---|---|---|---|---|---|---|
| 2009/0287206 A1 | 11/2009 | Jun | EP | 0086338 A1 | 8/1983 |
| 2009/0287236 A1 | 11/2009 | Bakos et al. | EP | 0286415 A2 | 10/1988 |
| 2009/0292164 A1 | 11/2009 | Yamatani | EP | 0589454 A2 | 3/1994 |
| 2009/0299135 A1 | 12/2009 | Spivey | EP | 0464479 B1 | 3/1995 |
| 2009/0299143 A1 | 12/2009 | Conlon et al. | EP | 0529675 B1 | 2/1996 |
| 2009/0299362 A1 | 12/2009 | Long et al. | EP | 0724863 B1 | 7/1999 |
| 2009/0299385 A1 | 12/2009 | Stefanchik et al. | EP | 0760629 B1 | 11/1999 |
| 2009/0299406 A1 | 12/2009 | Swain et al. | EP | 0818974 B1 | 7/2001 |
| 2009/0299409 A1 | 12/2009 | Coe et al. | EP | 1281356 A2 | 2/2003 |
| 2009/0306658 A1 | 12/2009 | Nobis et al. | EP | 0947166 B1 | 5/2003 |
| 2009/0306683 A1 | 12/2009 | Zwolinski et al. | EP | 0836832 B1 | 12/2003 |
| 2009/0322864 A1 | 12/2009 | Karasawa et al. | EP | 1402837 A1 | 3/2004 |
| 2009/0326561 A1 | 12/2009 | Carroll, II et al. | EP | 0744918 B1 | 4/2004 |
| 2010/0010294 A1 | 1/2010 | Conlon et al. | EP | 0931515 B1 | 8/2004 |
| 2010/0010298 A1 | 1/2010 | Bakos et al. | EP | 0941128 B1 | 10/2004 |
| 2010/0010299 A1 | 1/2010 | Bakos et al. | EP | 1411843 B1 | 10/2004 |
| 2010/0010303 A1 | 1/2010 | Bakos | EP | 1150614 B1 | 11/2004 |
| 2010/0010510 A1 | 1/2010 | Stefanchik | EP | 1477104 A1 | 11/2004 |
| 2010/0010511 A1 | 1/2010 | Harris et al. | EP | 1481642 A1 | 12/2004 |
| 2010/0023032 A1 | 1/2010 | Granja Filho | EP | 1493391 A1 | 1/2005 |
| 2010/0036198 A1 | 2/2010 | Tacchino et al. | EP | 0848598 B1 | 2/2005 |
| 2010/0048990 A1 | 2/2010 | Bakos | EP | 1281360 B1 | 3/2005 |
| 2010/0049190 A1 | 2/2010 | Long et al. | EP | 1568330 A1 | 8/2005 |
| 2010/0049223 A1 | 2/2010 | Granja Filho | EP | 1452143 B1 | 9/2005 |
| 2010/0056861 A1 | 3/2010 | Spivey | EP | 1616527 A2 | 1/2006 |
| 2010/0056862 A1 | 3/2010 | Bakos | EP | 1006888 B1 | 3/2006 |
| 2010/0057085 A1 | 3/2010 | Holcomb et al. | EP | 1629764 A1 | 3/2006 |
| 2010/0057108 A1 | 3/2010 | Spivey et al. | EP | 1013229 B1 | 6/2006 |
| 2010/0063538 A1 | 3/2010 | Spivey et al. | EP | 1721561 A1 | 11/2006 |
| 2010/0076451 A1 | 3/2010 | Zwolinski et al. | EP | 1153578 B1 | 3/2007 |
| 2010/0081877 A1 | 4/2010 | Vakharia | EP | 1334696 B1 | 3/2007 |
| 2010/0087813 A1 | 4/2010 | Long | EP | 1769766 A1 | 4/2007 |
| 2010/0113872 A1 | 5/2010 | Asada et al. | EP | 1836971 A2 | 9/2007 |
| 2010/0121362 A1 | 5/2010 | Clague et al. | EP | 1836980 A1 | 9/2007 |
| 2010/0130817 A1 | 5/2010 | Conlon | EP | 1854421 A2 | 11/2007 |
| 2010/0130975 A1 | 5/2010 | Long | EP | 1857061 A1 | 11/2007 |
| 2010/0131005 A1 | 5/2010 | Conlon | EP | 1875876 A1 | 1/2008 |
| 2010/0152539 A1 | 6/2010 | Ghabrial et al. | EP | 1891881 A1 | 2/2008 |
| 2010/0152609 A1 | 6/2010 | Zwolinski et al. | EP | 1902663 A1 | 3/2008 |
| 2010/0152746 A1 | 6/2010 | Ceniccola et al. | EP | 1477106 B1 | 6/2008 |
| 2010/0179510 A1 | 7/2010 | Fox et al. | EP | 1949844 A1 | 7/2008 |
| 2010/0179530 A1 | 7/2010 | Long et al. | EP | 1518499 B1 | 8/2008 |
| 2010/0191050 A1 | 7/2010 | Zwolinski | EP | 1709918 B1 | 10/2008 |
| 2010/0191267 A1 | 7/2010 | Fox | EP | 1985226 A2 | 10/2008 |
| 2010/0198005 A1 | 8/2010 | Fox | EP | 1994904 A1 | 11/2008 |
| 2010/0198149 A1 | 8/2010 | Fox | EP | 1707130 B1 | 12/2008 |
| 2010/0198244 A1 | 8/2010 | Spivey et al. | EP | 0723462 B1 | 3/2009 |
| 2010/0198248 A1 | 8/2010 | Vakharia | EP | 1769749 B1 | 11/2009 |
| 2010/0249700 A1 | 9/2010 | Spivey | EP | 1493397 B1 | 9/2011 |
| 2010/0286791 A1 | 11/2010 | Goldsmith | FR | 2731610 A1 | 9/1996 |
| 2010/0298642 A1 | 11/2010 | Trusty et al. | GB | 330629 A | 6/1930 |
| 2010/0312056 A1 | 12/2010 | Galperin et al. | GB | 2335860 A | 10/1999 |
| 2010/0331622 A2 | 12/2010 | Conlon | GB | 2403909 A | 1/2005 |
| 2011/0093009 A1 | 4/2011 | Fox | GB | 2421190 A | 6/2006 |
| 2011/0098694 A1 | 4/2011 | Long | GB | 2443261 A | 4/2008 |
| 2011/0098704 A1 | 4/2011 | Long et al. | JP | 56-46674 | 4/1981 |
| 2011/0105850 A1 | 5/2011 | Voegele et al. | JP | 63309252 A | 12/1988 |
| 2011/0112434 A1 | 5/2011 | Ghabrial et al. | JP | 4038960 A | 2/1992 |
| 2011/0115891 A1 | 5/2011 | Trusty | JP | 8-29699 A | 2/1996 |
| 2011/0124964 A1 | 5/2011 | Nobis | JP | 2002-369791 A | 12/2002 |
| 2011/0152609 A1 | 6/2011 | Trusty et al. | JP | 2003-088494 A | 3/2003 |
| 2011/0152610 A1 | 6/2011 | Trusty et al. | JP | 2003-235852 A | 8/2003 |
| 2011/0152612 A1 | 6/2011 | Trusty et al. | JP | 2004-33525 A | 2/2004 |
| 2011/0152858 A1 | 6/2011 | Long et al. | JP | 2004-065745 A | 3/2004 |
| 2011/0152859 A1 | 6/2011 | Long et al. | JP | 2005-121947 A | 5/2005 |
| 2011/0152878 A1 | 6/2011 | Trusty et al. | JP | 2005-261514 A | 9/2005 |
| 2011/0152923 A1 | 6/2011 | Fox | JP | 2006297005 A | 11/2006 |
| 2011/0160514 A1 | 6/2011 | Long et al. | NL | 1021295 C2 | 2/2004 |
| 2011/0190659 A1 | 8/2011 | Long et al. | SU | 194230 | 5/1967 |
| 2011/0190764 A1 | 8/2011 | Long et al. | SU | 980703 | 12/1982 |
| 2011/0245619 A1 | 10/2011 | Holcomb | WO | WO 84/01707 A1 | 5/1984 |
| 2011/0306971 A1 | 12/2011 | Long | WO | WO 92/13494 A1 | 8/1992 |
| | | | WO | WO 93/10850 A1 | 6/1993 |
| FOREIGN PATENT DOCUMENTS | | | WO | WO 93/20760 A1 | 10/1993 |
| DE | 3008120 A1 | 9/1980 | WO | WO 93/20765 A1 | 10/1993 |
| DE | 4323585 A1 | 1/1995 | WO | WO 95/09666 A1 | 4/1995 |
| DE | 19713797 A1 | 10/1997 | WO | WO 96/22056 A1 | 7/1996 |
| DE | 19757056 B4 | 8/2008 | WO | WO 96/27331 A1 | 9/1996 |
| DE | 102006027873 B4 | 10/2009 | WO | WO 96/39946 A1 | 12/1996 |

| | | |
|---|---|---|
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.

U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
International Preliminary Report on Patentability for PCT/US2009/053536, Feb. 15, 2011 (9 pages).
Zadno et al., "Linear Superelasticity in Cold-Worked NI-TI," Engineering Aspects of Shape Memory Alloys, pp. 414-419 (1990).
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
D.G. Fong et al., "Transcolonic Ventral Wall Hernia Mesh Fixation in a Porcine Model," Endoscopy 2007; 39: 865-869.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.

U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
Written Opinion for PCT/US2009/053536, Jan. 21, 2010 (9 pages).
U.S. Appl. No. 13/036,895, filed Feb. 28, 2011.
U.S. Appl. No. 13/036,908, filed Feb. 28, 2011.
U.S. Appl. No. 13/218,221, filed Aug. 25, 2011.
U.S. Appl. No. 13/267,251, filed Oct. 6, 2011.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/325,791, filed Dec. 14, 2011.
U.S. Appl. No. 13/352,495, filed Jan. 18, 2012.

* cited by examiner

STERILE APPLIANCE DELIVERY DEVICE FOR ENDOSCOPIC PROCEDURES

BACKGROUND

Endoscopy refers to looking inside the human body for medical reasons. Endoscopy may be performed using an instrument called an endoscope. Endoscopy is a minimally invasive diagnostic medical procedure used to evaluate the interior surfaces of an organ by inserting a small tube into the body, often, but not necessarily, through a natural body opening or through a relatively small incision. Through the endoscope, an operator may observe surface conditions of the organs, including abnormal or diseased tissue such as lesions and other surface conditions. The endoscope may have a rigid or a flexible tube and, in addition to providing an image for visual inspection and photography, the endoscope may be adapted and configured for taking biopsies, retrieving foreign objects, and introducing medical instruments to a tissue treatment region referred to as the work site. Endoscopy is a vehicle for minimally invasive surgery.

Laparoscopic surgery is a minimally invasive surgical technique in which operations are performed through small incisions (usually 0.5-1.5 cm), keyholes, as compared to larger incisions needed in traditional open-type surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

A key element in laparoscopic surgery is the use of a laparoscope: a telescopic rod lens system that is usually connected to a video camera (single-chip or three-chip). Also attached is a fiber-optic cable system connected to a "cold" light source (halogen or xenon) to illuminate the operative field, inserted through a 5 mm or 10 mm cannula to view the operative field. The abdomen is usually insufflated with carbon dioxide gas to create a working and viewing space. The abdomen is essentially blown up like a balloon (insufflated), elevating the abdominal wall above the internal organs like a dome. Carbon dioxide gas is used because it is common to the human body and can be removed by the respiratory system if it is absorbed through tissue.

Minimally invasive therapeutic procedures to treat diseased tissue by introducing medical instruments to a tissue treatment region through a natural opening of the patient are known as Natural Orifice Translumenal Endoscopic Surgery (NOTES)™. In general, there are a variety of systems for inserting an endoscope through a natural opening in the human body, dissecting a lumen, and then, treating the inside of the abdominal cavity. For example, in U.S. Pat. No. 5,297,536, which is incorporated by reference herein, a sample treatment system is disclosed. This system is comprised of a dissecting device for perforating a lumen wall; an endoscope insert member for inserting an endoscope, a tube, an endoscope, and a pneumoperitoneum device for insufflating the abdominal cavity; and a closing device.

When surgery of the inside of the abdominal cavity is carried out using this system, the endoscope insert member and tube are first inserted through a natural opening in the human body (mouth, anus, vagina, etc.) and the tube may be absorbed to a required organ wall by vacuum pressure, thus being fixed thereon. Next, a pneumoperitoneum needle is inserted and the abdominal cavity is insufflated. Then, the dissecting device is inserted and the organ wall is perforated. After surgery of the inside of abdominal cavity is complete, the perforation in the organ wall may be closed by an O-ring, and the endoscope and tube are withdrawn from the body.

Many different medical conditions, including hernias, may be addressed transluminally using endoscopic techniques. A hernia is a weakening of the musculofascial tissues defining the structural wall of a body cavity such as the abdomen, resulting in a gap through which tissues can protrude. Typically a sac is formed confining the tissues at the musculofascial defect, which protrudes from the plane of the tissue wall. There is a possibility of constriction of the neck of the sac, and life-threatening infection if the hernia remains untreated.

A weakening or separation of the musculofascial tissues due to any cause can develop into a hernia. For example scarring from a previous incision or other trauma of the abdominal wall can develop into a hernia, or a hernia can form at the site of a passage through the musculofascial tissue, the passage becoming enlarged, for example, due to pressure of the viscera during muscular exertion. There are various forms of hernias, the inguinal hernia being a common example wherein the abdominal viscera and peritoneal sac protrude through the floor of the inguinal cavity at the point where the musculofascial tissue is relatively weakened due to the passage of the spermatic duct (in males) or the femoral blood vessels and the round ligament (in females). Another common site of a hernia is the umbilicus. Hernias can also develop in the diaphragm, and elsewhere.

Another form of hernia is a ventral hernia. When a ventral hernia occurs, it usually arises in the abdominal wall where a previous surgical incision was made. In this area the abdominal muscles have weakened thereby resulting in a bulge or a tear. The inner lining of the abdomen pushes through the weakened area of the abdominal wall to form a balloon-like sac. A loop of intestines or other abdominal contents may be pushed into the sac.

Hernias have been repaired surgically by suturing across the musculofascial defect to draw the opposite sides of the defect together, the sutures bridging across the defect. However, such a repair is not suitable at hernias occurring at the site of a passage for ducts, blood vessels or the like. Moreover, pulling the sides of the defect inwardly results in tension on the musculofascial tissue via the sutures. The site of the sutures defines a weakening of the tissue and leads to a high rate of recurrence of the hernia at the sutured edge of a previous repair.

According to one technique for repairing hernias, a patch having sufficient strength to resist the tendency of the sac to protrude is placed over the defect and sutured to the musculofascial tissue. This technique avoids tension on the musculofascial tissues and has been shown to be successful in minimizing recurrence of the hernia. Various materials have been used in experimental or clinical hernia repairs, including for example polypropylene mesh, DACRON® fabric, tantalum gauze, and the like. Such technique may be performed using an open procedure which relies on cutting the abdominal section of the patient. The patch is placed in between the peritoneum and the skin. Besides having a relatively large incision site, the patch may eventually migrate through the peritoneum, for example, and adhere to the bowel.

Hernia repairs have been undertaken by laparoscopic techniques. With a laparoscopic technique, however, a plurality of smaller incisions must be made to the patient's abdominal section in order to introduce the various laparoscopic tools into the peritoneal cavity. Through the incisions, a patch may be introduced and attached to the inner abdominal wall to address the hernia. The patch is attached through various techniques, such as clips, sutures, or tacks. While less invasive then open-type surgery, the incisions, or ports, necessary for the laparoscopic procedure are susceptible to the formation of future ventral hernias.

Repairing a hernia transluminally through endoscopic techniques reduces the likelihood of recurring ventral hernias by eliminating the need to create external ports during the procedure. Using this technique, the endoscope, along with the necessary tools and devices, are introduced into the body via a natural orifice and then the hernia site is accessed transluminally. If a mesh patch is used to treat the hernia, it must be introduced to the hernia site while maintaining its sterilization.

Accordingly, in the field of endoscopy, there remains a need for improved methods and devices for delivering a sterile appliance, such as a mesh patch, to a surgical site while maintaining the sterilization of the appliance.

FIGURES

The novel features of the various embodiments are set forth with particularity in the appended claims. The various embodiments, however, both as to organization and methods of operation may best be understood by reference to the following description, taken in conjunction with the accompanying drawings as follows.

DESCRIPTION

Figure 1:
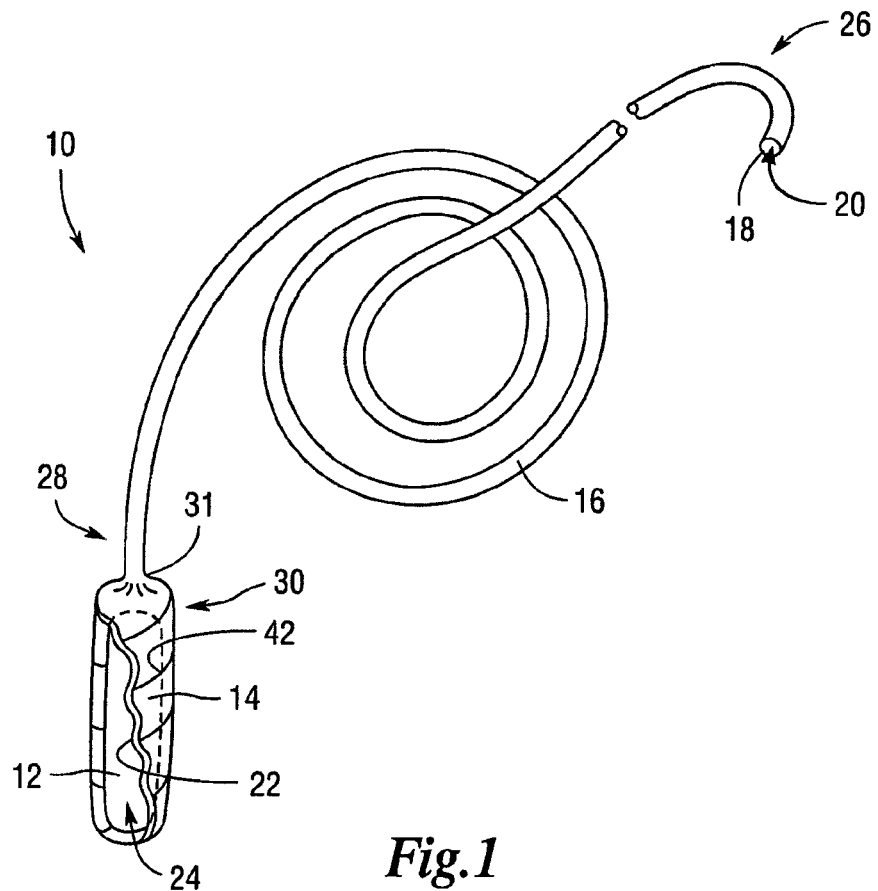
FIG. 1 is partial cross-sectional view of one embodiment of a delivery device.

FIG. 1 illustrates one embodiment of a surgical device 10. The surgical device 10 may be employed to deliver a sterile appliance 12 to a surgical site during an endoscopic procedure. The sterile appliance 12 may be any appliance, device, material, or structure that needs to be transported from outside a patient's body to inside the patient's body while maintaining a sterile state. In various embodiments, the sterile appliance 12 may be a mesh patch suitable for hernia repair. For example, the mesh patch may be a polypropylene and expanded polytetrafluoroethylene (ePTFE) hernia mesh, or other suitable mesh. The sterile appliance 12 also may include endoscopic clips or fasteners (not shown) for attaching the sterile appliance 12 to tissue. In other sample embodiments, the sterile appliance 12 may be a hemostatic pad.

The surgical device 10 also may be used in traditional laparotomy procedures as well as external noninvasive procedures to treat diseased or damaged tissue from outside the body. In one embodiment, the surgical device 10 may be configured to be positioned within a natural opening of the patient such as the mouth, anus, or vagina and subsequently advanced and positioned within internal body lumens such as the esophagus, colon, and/or uterus to reach the tissue treatment region or work site. Internal organs or cavities may be reached using trans-organ or trans-luminal surgical procedures. The surgical device 10 also may be configured to be positioned through a small incision or keyhole on the patient and can be passed through the incision to reach a tissue treatment region, cavity, or work site through a trocar. The treatment region may be located in various body lumens or organs such as the abdomen, esophagus, stomach, colon, liver, breast, brain, lung, and other organs or locations within the body.

In one embodiment, the surgical device 10 may be employed in conjunction with a flexible endoscope, such as the GIF-100 model available from Olympus Corporation. The flexible endoscope may be introduced into the patient trans-anally through the colon, orally through the esophagus, vaginally through the uterus, or the abdomen via an incision or keyhole and a trocar, for example. The endoscope assists the surgeon to guide and position the surgical device 10 near the tissue treatment region to treat diseased or damaged tissue in various body lumens and organs such as the abdomen, esophagus, stomach, colon, liver, breast, brain, lung, and other internal tissue treatment regions.

In one embodiment, the surgical device 10 comprises a container 14 and a tether 16. The container 14 may be of any suitable shape, such as cylindrical, spherical, teardrop, for example. In various embodiments, the container is dimensioned to fit through an endoscopic overtube. In one example embodiment the outer dimension of the container 14 does not exceed 14 mm in order to fit through a 14.5 mm overtube. An outer wall 22 of the container 14 defines a cavity 24. The cavity 24 is suitable for containing the sterile appliance 12. As may be appreciated by one of ordinary skill in the art, the container 14 may be constructed of any suitable material. In various embodiments, the container 14 may be comprised of a thin semiflexible plastic, such as polyethylene, polypropylene, polyurethane, or silicone. The container 14 also may be either clear, opaque, or a combination of both.

In the illustrated embodiment, the tether 16 is a hollow tube coupled to the container 14 with an outer wall 18 of the tether 16 defining a channel 20. The tether 16 has a proximal end 26 and a distal end 28. The distal end 28 is coupled to the container 14. As shown, the distal end 28 of the tether 16 is coupled to the proximal end 30 of the container 14 at a coupling 31. In other embodiments, the tether 16 may be coupled to a different portion of the container 14. In some embodiments, the tether 16 and the container 14 may be constructed from a unitary piece of material. Through the coupling 31, the channel 20 of the tether 16 is in fluid communication with the cavity 24 of the container 14. The tether 14 is generally flexible so as to allow navigation through the tortuous pathway of a body lumen during an endoscopic procedure. The tether 14 can be constructed from any suitable materials, such as polyvinyl chloride (PVC), silicone, TYGON®, or vinyl. In various embodiments, the tether 14 may be constructed with reinforcement, such as braiding or ribbing, to increase the strength of the tether 14. As appreciated by one of ordinary skill in the art, the outer diameter of the tether 14 may be of any suitable diameter.

Figure 2:
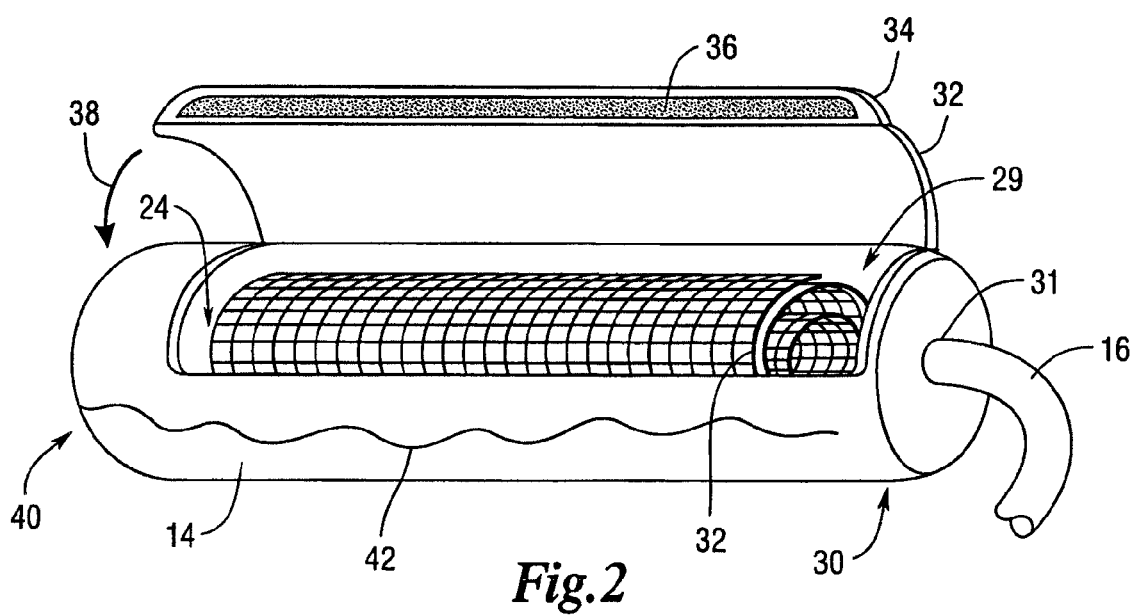
FIG. 2 is an enlarged view of the distal end of the surgical device shown in FIG. 1.

As shown in FIG. 2, the container 14 may include an opening 29. The opening 29 allows for the loading of the sterile appliance, shown as a mesh patch 32, into the cavity 24 of the container 14. As illustrated, the mesh patch 32 may be rolled into a cylinder-like formation before loading into the container 14. It should be appreciated that any suitable formation is acceptable.

The opening 29 may be defined by a door 32. The door 32 may further comprise a flap 34. In various embodiments, the flap 34 may contain an adhesive strip 36 used to seal the opening 29 when the door 32 is moved in direction 38. The opening 29 may also be located in any suitable location, such as near the proximal end 30 or the distal end 40 of the container 14. Furthermore, instead of using a door, other sealable configurations might be used, such as a screw cap or snap-fit connection, for example. Additionally, instead of using an adhesive strip 36, other suitable techniques for sealing may be used, such as a re-sealable zipper type connection, similar to a ZIPLOC® re-sealable zipper connection. In some embodiments a valve, such as a duckbill valve, will allow for the sterile appliance 12 to be loaded into the container 14.

Figure 3A:
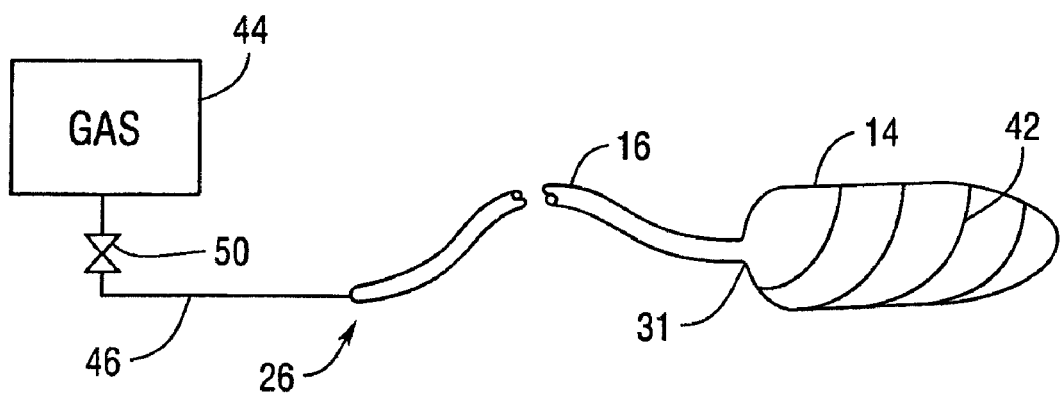
FIG. 3A illustrates one embodiment of a delivery device system.
Figure 3B:
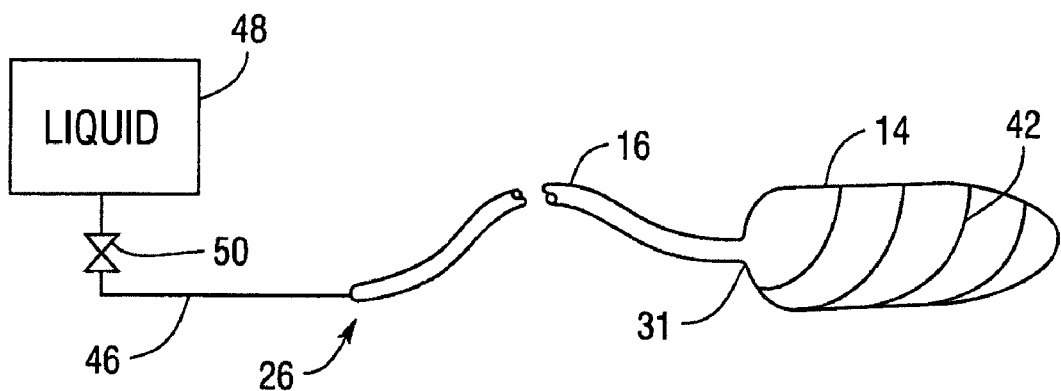
FIG. 3B illustrates one embodiment of a delivery device system.
Figure 3C:
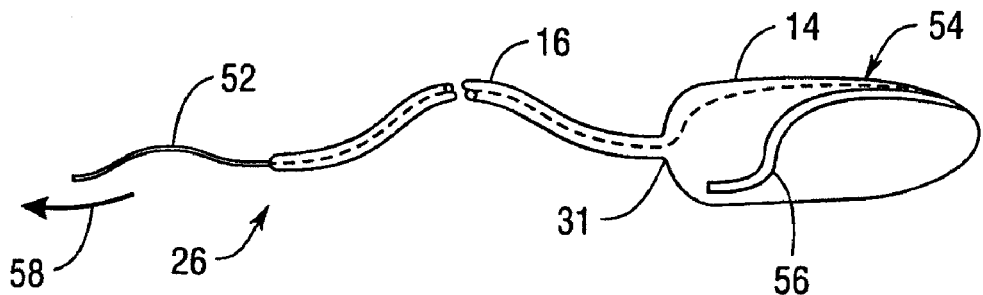
FIG. 3C illustrates one embodiment of a delivery device.

The container 14 may comprise at least one seal 42, or otherwise structurally weakened area, such as a groove or indention, for example. The seal 42 may be in any configuration. For instance, the seal 42 may be a spiral (FIG. 1) or wavy (FIG. 2), straight, or a combination of various configurations. When the seal 42 opens, the contents of the container 14, such as the mesh patch 32, are released from the cavity 24. Any suitable technique may be utilized to open the seal 42. Examples of suitable sealing techniques are shown in FIGS. 3A-3C. In FIG. 3A a gas 44 is introduced to the channel 20 of the proximal end 26 of the tether 14 via a line 46. The gas 44 may be, for example, carbon dioxide, room air, or helium. The flow of the gas 44 may be controlled by a valve 50 located in the line 46. The gas 44 travels through the channel 20 and enters the cavity 24 through the coupling 31. As more of the gas 44 is introduced into the cavity 24 via the tether 16, the air pressure in the cavity 24 increases. The outwardly expanding force caused by the increase in air pressure eventually causes the container 14 to open or separate at the seal 42. Once the container 14 opens, the contents of the container 14 are released. In various embodiments, once the seal 42 separates, the opened (or exploded) container 14 remains connected to the tether 16 at the coupling 31. As may be readily understood by one of ordinary skill in the art, the tether 16 should be constructed to withstand higher air pressures than the seal 42.

As shown in FIG. 3B a liquid 48 may be introduced into the channel 20 at the proximal end 26 of the tether 14 via a line 46. The liquid 48 may be, for example, saline or BETADINE®. The flow of the liquid 48 may be controlled by a valve 50 located in the line 46. The liquid 48 travels through the channel 20 and enters the cavity 24 at the coupling 31. As more of the liquid 48 is introduced into the cavity 24 via the tether 16, the liquid pressure in the cavity 24 increases. The force caused by the increase in liquid pressure eventually causes the container 14 to open or separate at the seal 42. Once the container 14 opens, the contents of the container 14 are released. In various embodiments, once the container 14 opens, the opened (or exploded) container 14 remains connected to the tether 16 at the coupling 31. As understood by one of ordinary skill in the art, the tether 16 should be constructed to withstand higher liquid pressures than the seal 42. Furthermore, in various embodiments, a combination of the gas 44 and the liquid 48 may be used to open the seal 42 of the container 14.

As shown in FIG. 3C a cable 52 may be used to apply the necessary force to open the seal 42 on the container 14. As illustrated, the cable 52 may protrude from the proximal end 26 of the tether 16, and also extend towards the container 14 through the channel 20 of the tether 16. The distal end 54 of the cable 52 may be coupled to a ripcord-type seal 56 embedded in the outer wall 22 of the container 14. Similar to the seal 42, the ripcord-type seal 56 may be configured in any suitable configuration, such as a spiral, a curve, straight, wavy, or any combination thereof. As a user, such as a surgeon or medical technician, imparts a force 58 in the proximal direction, longitudinal to the cable 52, the distal end 54 of the cable pulls on the embedded ripcord-type seal 56 and causes it to open. Once open, the contents of the container 14, such as the mesh patch 32, are thereby released.

Figure 4A:
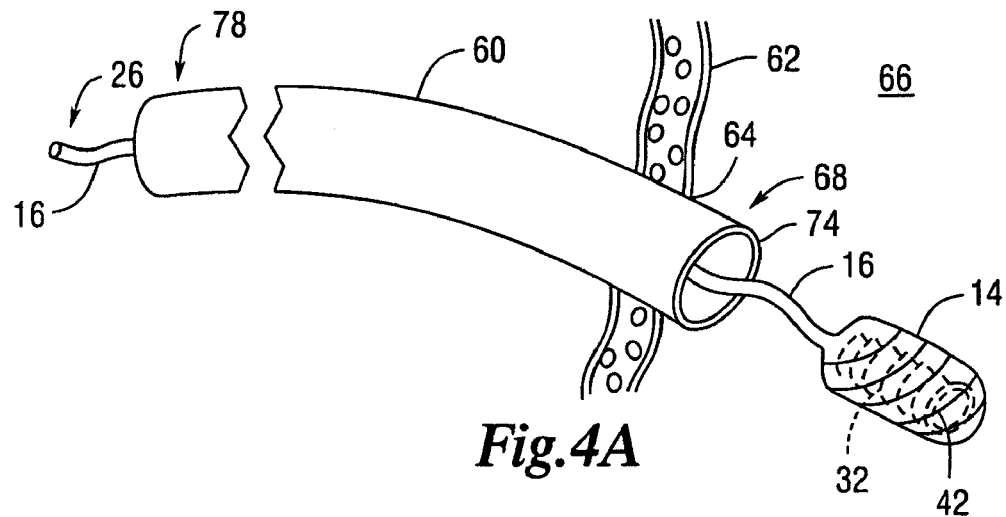
FIG. 4A is a view the delivery device shown in FIG. 1 used with an overtube.
Figure 4B:
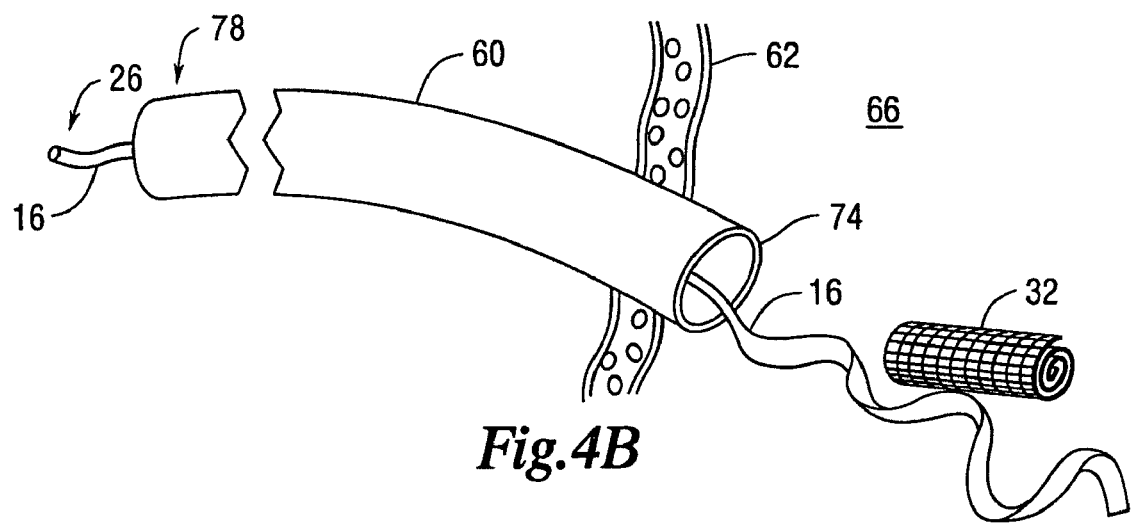
FIG. 4B is a view the delivery device shown in FIG. 1 used with an overtube.
Figure 4C:
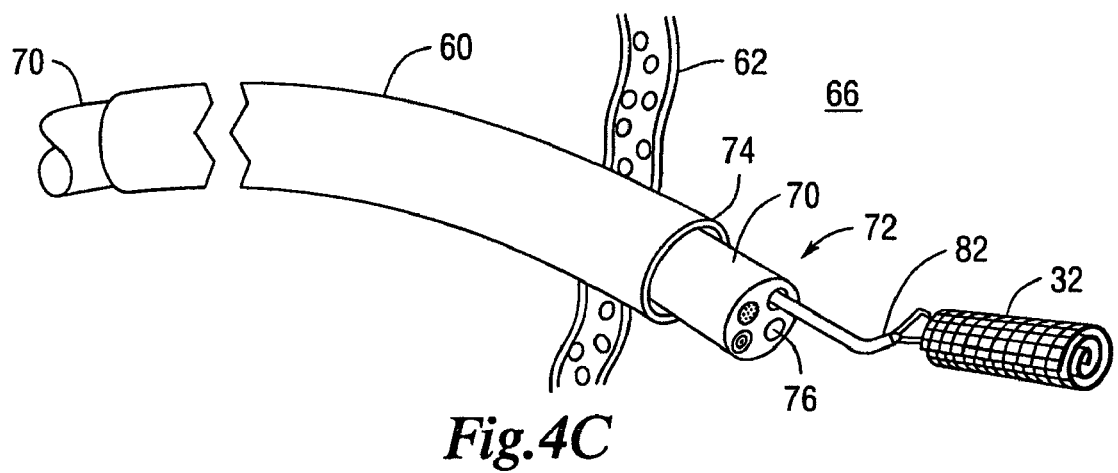
FIG. 4C is a view the delivery device shown in FIG. 1 used with an overtube.

The progression of the operation of an embodiment of the surgical device 10 is shown in FIGS. 4A-4C. The illustrated embodiment shows the surgical device 10 used in connection with a transluminal endoscopic procedure. As shown in FIG. 4A a distal end 68 of an overtube 60 is inserted through a tissue wall 62 via a port 64 in order to reach a body cavity 66. The tissue wall 62 may be part of, for example, the stomach, the colon, or the uterus. The proximal end 78 of the overtube 60 may be located outside the patient's body at a natural orifice, such as the mouth or colon. As understood by one of ordinary skill in the art, an endoscope, or other endoscopic tools and devices, could be inserted into the proximal end 78 of the overtube 60 and passed through the overtube 60 in order to access the body cavity 66. As illustrated, the container 14 of surgical device 10 may be passed through the overtube 60 and into the body cavity 66. In various embodiments, the surgical device 10 may be inserted into the proximal end 78 of the overtube 60. Once inserted into the overtube 60, an endoscope 70 (FIG. 4C) may be inserted into the proximal end 78 of the overtube 60. As the endoscope 70 is fed through the overtube 60, a distal end 72 will push the container 14 through the overtube 60 and into the body cavity 66. In various embodiments, the tether 16 may be located in between the wall 74 of the overtube 60 and the endoscope 70. In other embodiments, the tether 16 may be backfed through a lumen, or working channel 76 of the endoscope 70. As may be readily understood by those of ordinary skill in the art, any suitable technique can be used to move the container 14 from the proximal end 78 of the overtube to the body cavity 66.

In various embodiments of the present method and system, the proximal end 26 of the tether 16 remains outside the patient's body, protruding from the proximal end 78 of the overtube 60. Once positioned in the desired location, such as the body cavity 66, a force can be applied to the container 14 through the proximal end 28 of the tether 16. If liquid or gas is used to deliver the force, once the cavity 24 has reached a sufficient pressure, the seal 42 will rupture. As shown in FIG. 4B, once the seal ruptures the contents of the container 14, such as the mesh patch 32, are released into the body cavity 66. Once the contents are released, the user may remove the exploded container 14 from the body cavity 66 by pulling the tether 16 and the exploded container 14 through the overtube 60. If the seal 42 is formed in a spiral, the container 14 may become ribbon-like once the seal 42 is ruptured. The user could then pull on the proximal end 26 of the tether 16 to remove the ribbon from the body cavity 66 and the overtube 60. If the tether 16 had been backfed into the lumen 76 of endoscope 70, the user may pull the tether 16 and the exploded container 14 through the lumen 76. As shown in FIG. 4C, once the contents of the container 16 have been released, the operator may then introduce tools, such as a pair of graspers 82, to position the mesh patch 32 at the desired location within the body cavity 66.

Figure 5A:
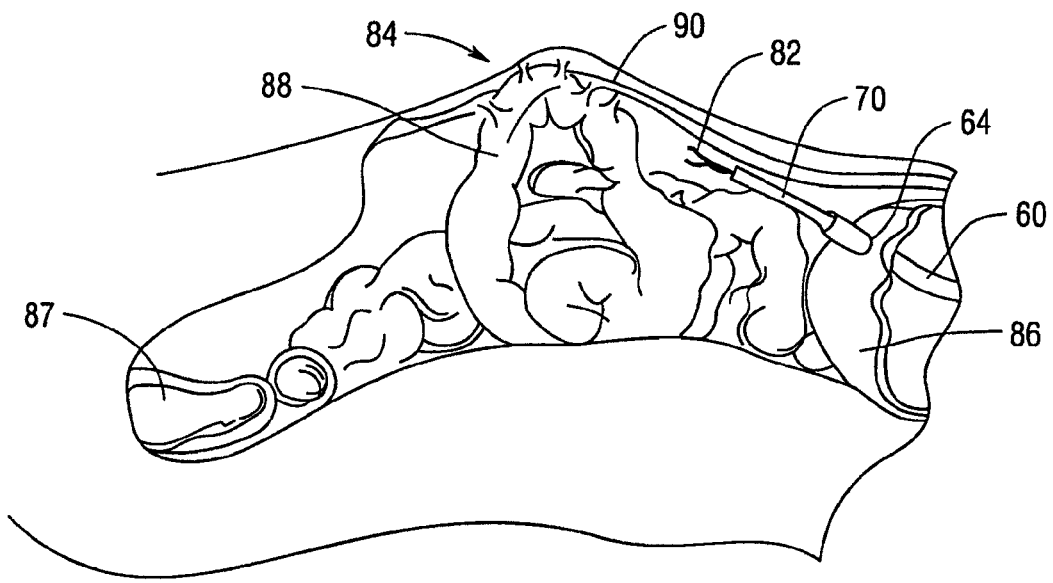
FIG. 5A is partial cross-sectional view of a body cavity and endoscope used during a hernia repair surgical procedure.

FIGS. 5A-5D show the surgical device 10 used in connection with a transluminal endoscopic hernia mesh fixation procedure. As illustrated in the example embodiment, the hernia site 84 is accessed through the patient's stomach 86. As may be appreciated by one of ordinary skill in the art, the hernia site 84 also could be reached from a variety of other locations, such as the colon 86 or the uterus (not shown). In FIG. 5A, a portion of the intestine 88 is shown adherent to the anterior abdominal wall 90 and bulging through a previous incision site. After the overtube 60 has been inserted through a port 64 in the stomach 86, an endoscope 70 may be introduced to the hernia site 88 in order to survey the site. Tools, such as the pair of graspers 82, also may be used to dissect any adhesions that may be present. In various embodiments, the operator may use the endoscope 70 to observe the hernia site 84 to determine the size and/or type of patch necessary to fix the torn or damaged tissue.

Figure 5B:
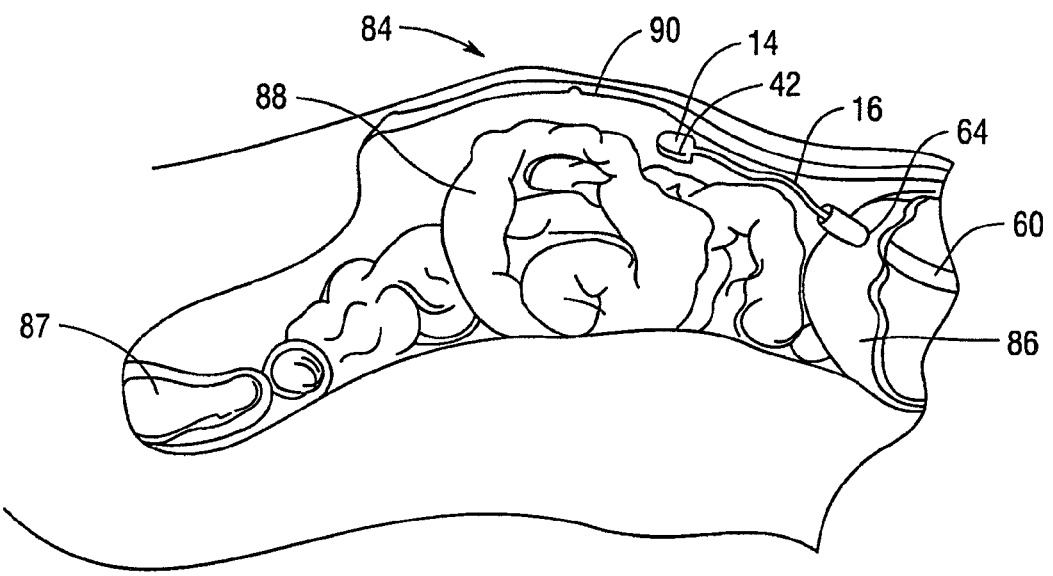
FIG. 5B is partial cross-sectional view of a body cavity illustrating the delivery device shown in FIG. 1 used during a hernia repair surgical procedure.
Figure 5C:
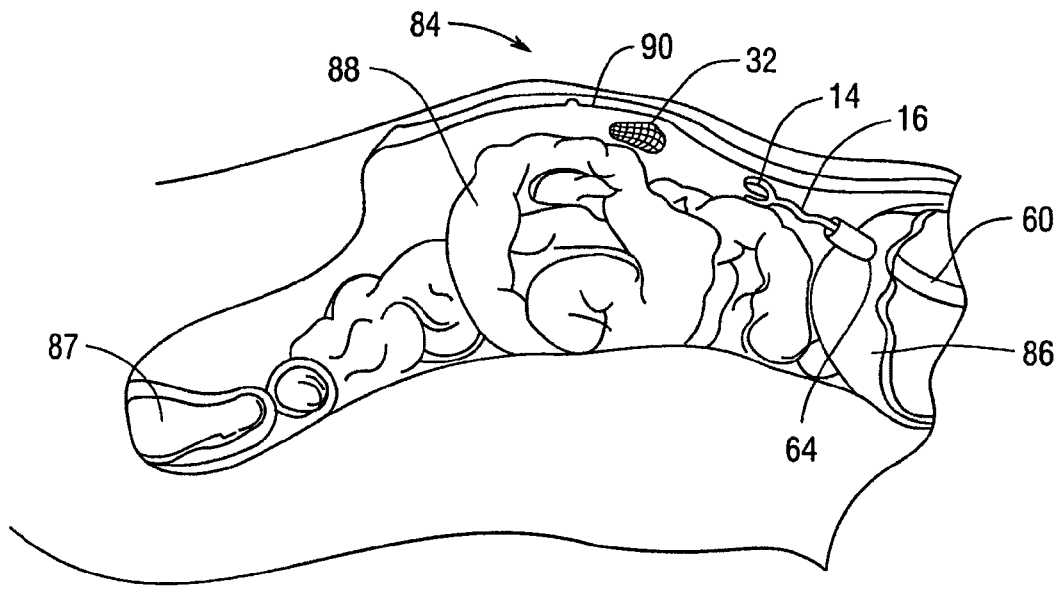
FIG. 5C is partial cross-sectional view of a body cavity illustrating the delivery device shown in FIG. 1 used during a hernia repair surgical procedure.
Figure 5D:
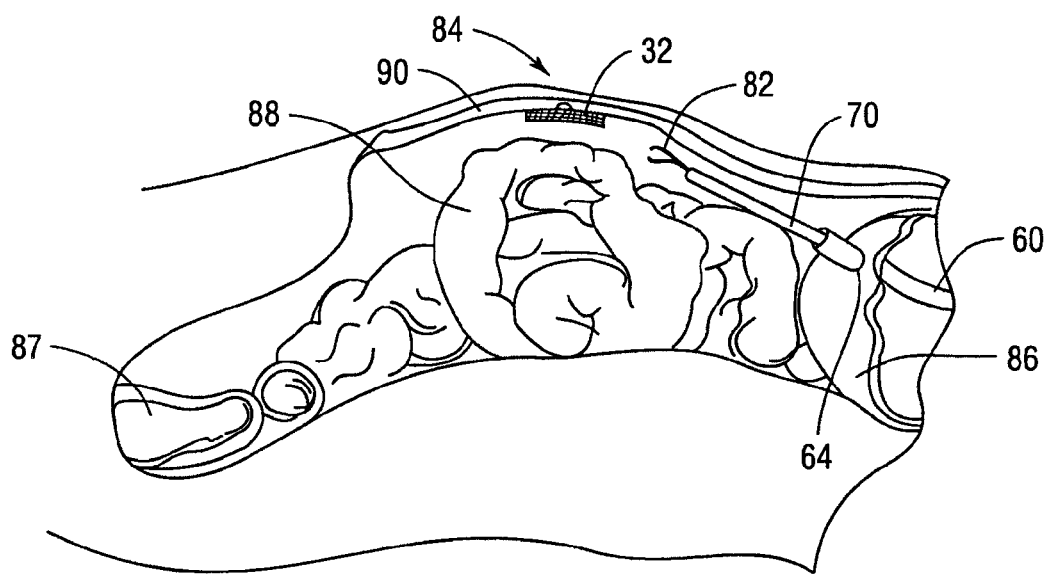
FIG. 5D is partial cross-sectional view of a body cavity and endoscope used during a hernia repair surgical procedure.

As shown in FIG. 5B, once the container 14 is loaded with the sterile mesh patch 32, the container 14 is introduced to the hernia site 84 through the overtube 60. The container 14 may be passed through the overtube 60 using any suitable technique. Once in position, a force (such as air pressure, liquid pressure, mechanical force) is applied to the container in order to open the seal 42. Once the seal 42 is opened, the mesh patch 32 is released into the body cavity near the hernia site 84 (FIG. 5C). The exploded container 14 then may be removed from the body cavity through the overtube 60. The endoscope 70 may then be introduced to the hernia site 84 through the overtube 60. Tools, such as graspers 82, may be used to attach the mesh patch 32 to the anterior abdominal wall 90 (FIG. 5D).

Using the surgical device, a sterile appliance, such as a mesh patch, can be delivered from a sterile field outside the body to a desired body cavity while maintaining a sterile state. Once placed in the proper location, the sterile appliance can be released and manipulated accordingly.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by the cleaning or replacement of particular pieces, and subsequent reassembly. In particular, the device can be disassembled, and any number of the particular pieces or parts of the device can be selectively replaced or removed in any combination. Upon the cleaning and/or replacement of particular parts, the device can be reassembled for subsequent use either at a reconditioning facility or by a surgical team immediately prior to a surgical procedure. Those skilled in the art will appreciate that the reconditioning of a device can utilize a variety of techniques for disassembly, cleaning/replacement, and reassembly. The use of such techniques, and the resulting reconditioned device, are all within the scope of the present application.

Preferably, the various embodiments described herein will be processed before surgery. First, a new or used device is obtained and, if necessary, cleaned. The instrument can then be sterilized. In one sterilization technique, the device is placed in a closed and sealed container, such as a plastic or TYVEK® bag. The container and device are then placed in a field of radiation that can penetrate the container, such as gamma radiation, x-rays, or high-energy electrons. The radiation kills bacteria on the instrument and in the container. The sterilized device can then be stored in the sterile container. The sealed container keeps the instrument sterile until it is opened in the medical facility. It is preferred that the device is sterilized. This can be done by any number of ways known to those skilled in the art, including beta or gamma radiation, ethylene oxide, or steam.

Although the various embodiments have been described herein in connection with certain disclosed embodiments, many modifications and variations to those embodiments may be implemented. Also, where materials are disclosed for certain components, other materials may be used. The foregoing description and following claims are intended to cover all such modifications and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A surgical device, comprising:
   a container dimensioned to fit in an endoscopic overtube, the container comprising a seal in the shape of a spiral;
   a hollow tether having a proximal end and a distal end, the distal end coupled to the container;
   wherein the container comprises a cavity dimensioned to house a sterile appliance, wherein the cavity is structured to open responsive to a force applied through the hollow tether; and
   wherein the force is air pressure.

2. A surgical device, comprising:
   a container dimensioned to fit in an endoscopic overtube, the container comprising a seal in the shape of a spiral;
   a hollow tether having a proximal end and a distal end, the distal end coupled to the container;
   a sterile appliance, the sterile appliance housed within the container;
   wherein the container is structured to open responsive to a force applied through the hollow tether and release the sterile appliance; and
   wherein the force is air pressure.

3. The device of claim 2, wherein the sterile appliance is a mesh sheet.

4. The device of claim 2, wherein the sterile appliance is a hemostatic pad.

5. A surgical device, comprising:
   a container dimensioned to fit in an endoscopic overtube, the container having a seal in the shape of a spiral and a sterile cavity defined by an outer wall;
   a tether having an outer wall, a proximal end and a distal end, the outer wall defining a channel, wherein the channel is in fluid communication with the cavity;
   a mesh patch, the mesh patch housed within the container;
   wherein the container is structured to open responsive to a force applied through the tether at the proximal end and open the seal to release the mesh patch, and
   wherein the force is air pressure.

6. The device of claim 5, wherein the container is less than 14.5 mm in diameter.

7. The device of claim 6, wherein container comprises a sealable opening suitable to load the mesh patch into the sterile cavity.

8. A method for using a surgical device, comprising:
inserting a container into a body cavity during a natural orifice translumenal endoscopic surgical procedure, wherein the container houses a sterile hernia patch, and wherein the container comprises a seal in the shape of a spiral;
applying a force through a tether coupled to the container to open the container in the body cavity, wherein the force is air pressure;
releasing the sterile hernia patch from the container into the body cavity; and removing the container from the body cavity.

9. A surgical device, comprising:
a container dimensioned to fit in an endoscopic overtube, the container comprising a seal in the shape of a spiral;
a hollow tether having a proximal end and a distal end, the distal end coupled to the container;
wherein the container comprises a cavity dimensioned to house a sterile appliance, wherein the cavity is structured to open responsive to a force applied through the hollow tether; and
wherein the force is liquid pressure.

10. A surgical device, comprising:
a container dimensioned to fit in an endoscopic overtube, the container comprising a seal in the shape of a spiral;
a hollow tether having a proximal end and a distal end, the distal end coupled to the container;
a sterile appliance, the sterile appliance housed within the container;
wherein the container is structured to open responsive to a force applied through the hollow tether and release the sterile appliance; and
wherein the force is liquid pressure.

11. The device of claim 10, wherein the sterile appliance is a mesh sheet.

12. The device of claim 10, wherein the sterile appliance is a hemostatic pad.

13. A surgical device, comprising:
a container dimensioned to fit in an endoscopic overtube, the container having a seal in the shape of a spiral and a sterile cavity defined by an outer wall;
a tether having an outer wall, a proximal end and a distal end, the outer wall defining a channel, wherein the channel is in fluid communication with the cavity;
a mesh patch, the mesh patch housed within the container;
wherein the container is structured to open responsive to a force applied through the tether at the proximal end and open the seal to release the mesh patch; and
wherein the force is liquid pressure.

14. The device of claim 13, wherein the container is less than 14.5 mm in diameter.

15. The device of claim 13, wherein container comprises a sealable opening suitable to load the mesh patch into the sterile cavity.

16. A method for using a surgical device, comprising:
inserting a container into a body cavity during a natural orifice translumenal endoscopic surgical procedure, wherein the container houses a sterile hernia patch, and wherein the container comprises a seal in the shape of a spiral;
applying a force through a tether coupled to the container to open the container in the body cavity, wherein the force is liquid pressure;
releasing the sterile hernia patch from the container into the body cavity; and
removing the container from the body cavity.

* * * * *